United States Patent
Brau

(12) 
(10) Patent No.: US 6,296,609 B1
(45) Date of Patent: Oct. 2, 2001

(54) SURGICAL RETRACTOR AND RELATED SURGICAL APPROACH TO ACCESS THE ANTERIOR LUMBAR REGION

(76) Inventor: Salvador A. Brau, 110 Tigertrail Rd., Los Angeles, CA (US) 90049

(*) Notice: Subject to any disclaimer, the term of this patent is extended or adjusted under 35 U.S.C. 154(b) by 0 days.

(21) Appl. No.: 09/549,973

(22) Filed: Apr. 14, 2000

(51) Int. Cl.[7] .................................................... A61B 1/32
(52) U.S. Cl. ............................................................ 600/210
(58) Field of Search ................................. 600/210, 206, 600/231, 233, 232; 433/140

(56) References Cited

U.S. PATENT DOCUMENTS

| | | |
|---|---|---|
| D. 343,235 | 1/1994 | LeVahn . |
| D. 343,236 | 1/1994 | Quigley et al. . |
| 3,965,890 * | 6/1976 | Gauthier ................................. 600/210 |
| 3,998,217 | 12/1976 | Trumbull et al. . |
| 4,481,947 * | 11/1984 | Chaster ................................. 600/210 |
| 4,610,243 * | 9/1986 | Ray ....................................... 600/206 |
| 4,616,633 * | 10/1986 | Garcia ................................... 600/206 |
| 4,747,395 | 5/1988 | Brief . |
| 4,813,401 | 3/1989 | Grieshaber . |
| 4,817,587 * | 4/1989 | Janese ................................... 600/210 |
| 4,995,875 * | 2/1991 | Coes ...................................... 600/210 |
| 5,025,780 | 6/1991 | Farley . |
| 5,052,373 | 10/1991 | Michelson . |
| 5,351,680 | 10/1994 | Jung . |
| 5,688,223 | 11/1997 | Rosendahl . |
| 5,728,046 | 3/1998 | Mayer et al. . |

(List continued on next page.)

OTHER PUBLICATIONS

G. Mosser Taylor M.D., "A Simple Retractor for Spinal Surgery", The Journal of Bone and Joint Surgery, vol. 20, No. 1, pp. 183–184, Jan. 1946.*

Selected pages from Allegiance web site via the Internet (See attached).
Selected pages from Spectrum web site via the Internet (See attached).
"Vascular Injury In Anterior Lumbar Surgery," Spine, Nov. 1993, vol. 18, No. 15, pp. 2227–2230.

*Primary Examiner*—Jeffrey A. Smith
*Assistant Examiner*—Eduardo C. Robert
(74) *Attorney, Agent, or Firm*—Christie, Parker & Hale, LLP

(57) ABSTRACT

An instrument and method for exposing a selected area of the anterior lumbar region for a surgical procedure on the spine comprising making an incision on a human or animal body that exposes the anterior rectus sheath of the left rectus muscle, cutting the anterior rectus sheath to expose the body of the rectus muscle, and mobilizing the rectus muscle along its length by at least 3 cm in both directions from the site of the sheath incision. The rectus is then retracted medially, and the posterior rectus sheath is incised to expose the peritoneum. The peritoneum is pushed aside and tissues between the surgeon and the psoas muscle are dissected away. The ureter and the left iliac vessels are mobilized so that they are retractable from the dissected field, then the rectus muscle is moved laterally and a retractor is inserted into the dissected field. The retractor comprises a handle portion and an elongated blade portion having a first end connected to the handle portion, and having a substantially flat configuration which generally extends at an angle relative to the handle and below an axis aligned with the handle when the retractor is in use in surgery. The blade portion also has a second end spaced from the handle portion and shaped as a lip which curves in a direction away from the handle portion. The lip projects to a remote end spaced less than about 2 cm from a plane defined by the blade portion adjacent to the lip. The retractor is stabilized by engaging the lateral aspect of a vertebral body or disc with the lip of the retractor and retracting the tissues with the blade portion to expose the selected vertebral area.

18 Claims, 5 Drawing Sheets

U.S. PATENT DOCUMENTS

| | | | |
|---|---|---|---|
| 5,743,853 | * | 4/1998 | Lauderdale ............................ 600/210 |
| 5,755,660 | * | 5/1998 | Tyagi ................................... 600/232 |
| 5,795,291 | | 8/1998 | Koros et al. . |
| 5,902,233 | | 5/1999 | Farley et al. . |
| 5,931,777 | | 8/1999 | Sava . |
| 5,944,658 | | 8/1999 | Koros et al. . |
| 5,971,920 | * | 10/1999 | Nagel ................................... 600/206 |
| 5,984,865 | | 11/1999 | Farley et al. . |
| 6,152,874 | * | 11/2000 | Looney et al. ....................... 600/214 |

* cited by examiner

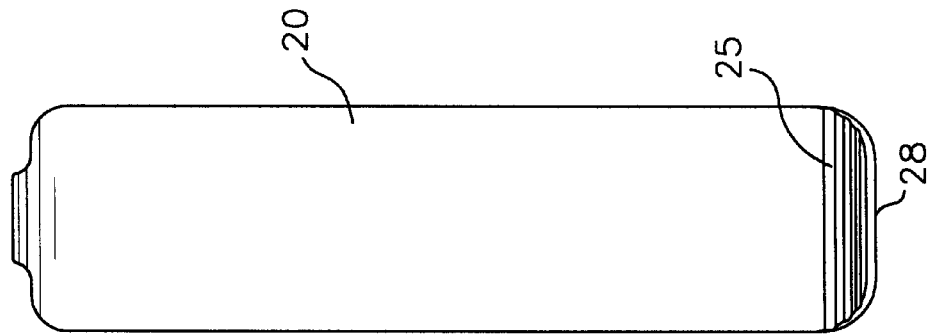
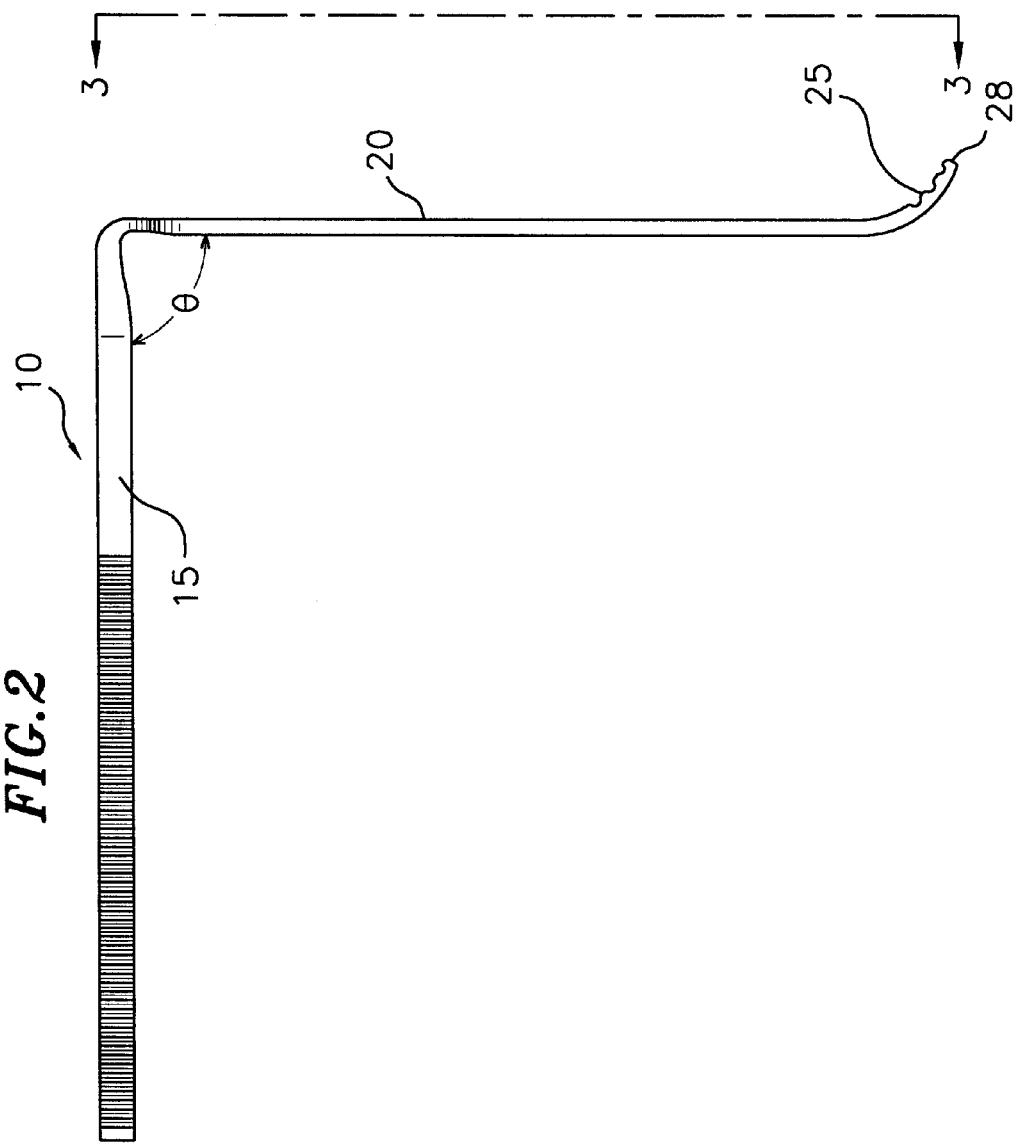

SURGICAL RETRACTOR AND RELATED SURGICAL APPROACH TO ACCESS THE ANTERIOR LUMBAR REGION

BACKGROUND OF THE INVENTION

Spine surgery, such as vertebral fusions, is common and is becoming more reliable as better methods are developed for stabilizing the back and improving bone grafts, for example, to repair disc injuries, vertebral fractures, and the effects of osteoarthritis. Many spine surgeries require an anterior approach, such as those for degenerative disc disease (both de novo and to correct failed prior back surgery), for infected discs, tumor removal and scoliosis (e.g., for excision, drainage, or decompression).

Anterior fusions are often preferable to posterior fusions because the bone surface area available for the fusion is considerably larger and any discs to be removed are more accessible. This makes the likelihood of successful fusion greater and the time required for the operation less, translating to less time that the patient is under general anesthesia. For example, since the introduction of threaded devices for Anterior Lumbar Interbody Fusion (ALIF), this procedure has become quite popular in the treatment of degenerative disc disease and chronic spinal instability as well as in failed posterior arthrodesis attempts. The procedure, however, is heavily dependent on the ability of the approach surgeon to provide exposure quickly and safely in view of a reported incidence of vascular injury as high as 15% (Baker et al., Spine 1993; 18:2227–2230) and a 2.3% incidence of retrograde ejaculation (Regan et al., Spine 1999; 24:402–11). The requirement of a direct anterior-posterior exposure for alignment of the devices has presented a significant challenge to provide a small incision and yet maintain the degree of safety necessary to prevent injury to the iliac vessels and the autonomic nerve plexus.

Generally, there are two anterior approaches for clearing a surgical field for the anterior lumbar region currently in use. One is the paramedian rectus splitting anterior retroperitoneal approach and the other is the lateral muscle splitting retroperitoneal approach. Both of these approaches have the disadvantage that they damage the muscles through which the surgeon must go to access the retroperitoneal space. Damaged muscle can lead to increased analgesic requirements during recovery, hernias, and loss of muscle function in the patient. Additionally, these approaches may require a large incision, leading to increased trauma to the skin, abdominal muscles, and internal structures. This can increase the subsequent pain for the patient, which requires additional post-operative management, while increasing recovery time. Procedures that entail or result in penetration of the peritoneum also lead to increased risk to the patient, for example, through damage to peritoneal organs, subsequent adhesions, infection, and the like.

Likewise, many surgical instruments are used once the field has been cleared to allow the spine surgeon access to the lumbar region. Retractors are used to secure the area open during the spine surgery. A variety of retractors and blades, and other implements such as Steinman pins, have been used for this purpose (see, e.g., U.S. Pat. Nos. 3,998, 217, 4,813,401, 5,025,780, 5,052,373, 5,688,223, 5,728,046, 5,795,291, 5,902,233, 5,944,658). While these retractors and implements help keep the area open and the tissue retracted, they suffer from several disadvantages. For example, standard retractor blades can slip out of place, or allow the peritoneum, peritoneal contents, nerves, vessels, or ureter to escape into the field of the surgery, risking injury to these structures. Hand-held retractors increase this risk. Pins are sometimes inserted into the vertebral body to hold back vessels and nerves, but they carry a great risk during deployment of the very damage the surgeon seeks to prevent. In lumbar region spine surgery, vascular injury, often perforation of the iliac vein and/or artery is the most common and severe complication. Other issues with the surgical instruments commonly used includes the size of the retractors, which may require a large incision in order to be placed correctly and to allow the spine surgeon a large enough field in which to work.

A need exists for an instrument and anterior retroperitoneal approach that permits rapid surgical access to the desired lumbar area, permits a small incision, and is stable and safe during subsequent procedures.

SUMMARY OF THE INVENTION

The present invention provides a retractor blade and surgical access method that fulfill the need for rapid lumbar access, a small incision, and reduced risk of bleeding/accidental vascular injury, nerve injury, or ureter injury. The invention also provides a secure and stable open position even during bone routing, drilling, and screwing.

The invention features a retractor instrument for maintaining a clear surgical field which comprises a handle portion and an elongated blade portion having a first end connected to the handle portion and a second end region spaced from the handle portion and shaped as a lip that curves in a direction away from the handle portion when the blade portion is in the operable configuration. The blade portion extends substantially along its entire length below an axis aligned with the handle and generally at an angle relative to the handle portion when the instrument is in an operable configuration. The lip portion of the blade takes up no more than about 20% of the blade length, preferably no more than about 15%, and most preferably no more than about 10%. The lip projects to a leading edge spaced less than about 2 cm from a plane defined by the blade portion immediately adjacent to the curvature of the lip, and is of a shape and size sufficient to engage the lateral aspect of a vertebral body or vertebral disc when the blade portion is positioned adjacent to and substantially perpendicular to the vertebra and/or a disc. The lip of the blade has the advantage that it can securely engage the lateral aspect of a vertebral body, something that retractors not having this lip cannot do, and this secure engagement offers greatly improved retraction without tissue slipping into the surgical field. The lip also eliminates the need to have channels on the blade used to introduce sharp pins to secure the blade to the vertebral body. Those pins can actually cause damage if not secured properly.

They also require wider exposure for proper placement and fail to provide lateral exposure for protection against vessel damage. Likewise, the lip itself does not have any sharp protrusions, which could cause tissue damage.

The blade of the retractor is preferably substantially flat in a rigid embodiment, or can be somewhat curved in a malleable embodiment, and the blade is preferably at an angle from about 80° to 150° to the handle when the retractor is in use. The angle is measured below an axis aligned with the handle. The lip at the distal end of the blade is at least 0.5 cm long and curves at least 0.3 cm from the plane of the blade, and is preferably roughened. Preferably, the lip has a radius of curvature of between about 1 cm and 3 cm and the curve of the lip extends between about 20° and 50° of the circle of curvature. The length of the blade portion is sufficient to reach the vertebral region from the anterior side of the body it is being used on. The width of the blade is preferably between 0.5–2.5 inches, more preferably between 1–2 inches, and most preferably between about 1.25–1.5 inches. The width is important to protect against vessel damage, as in typical lumbar exposures, the space between the major vessels and the vertebral body is very limited and to use retractors with widths over about 2 inches risks stretching or otherwise damaging the vessels.

The invention also features a method of clearing an anterior lumbar region surgical field comprising making an incision on a body needing surgery that exposes the anterior rectus sheath of the left rectus muscle; cutting the anterior rectus sheath to expose the body of the rectus muscle; mobilizing the rectus muscle along its length by at least 3 cm in both directions from the site of the sheath incision, and retracting the rectus medially; cutting the posterior rectus sheath to expose the peritoneum; pushing aside the peritoneum and dissecting away any intervening tissues to expose the psoas muscle; mobilizing the ureter and the left iliac vessels so that they are retractable from the dissection field; and retracting the rectus muscle laterally, the peritoneum, ureter, vessels, and intervening tissues to provide a clear anterior lumbar region surgical field. This surgical procedure has the advantage that it does not damage the rectus muscle, nor does it perforate the peritoneum, so recovery for the patient is made much easier and faster, and the risk of complications is reduced.

Another feature of the invention is a method of exposing a selected area of the anterior lumbar region for a surgical procedure on that region comprising the steps in the above paragraph to expose the anterior lumbar region, and then retracting the rectus muscle laterally; inserting a retractor into the dissected field, the retractor comprising a handle portion and an elongated blade portion having a first end connected to the handle portion, the blade portion having a substantially flat configuration which generally extends at an angle relative to the handle, the blade portion having a second end spaced from the handle portion and shaped as a lip which curves in a direction away from the handle portion. The retractor is stabilized by engaging the lateral aspect of a vertebral body or disc with the lip of the retractor and retracting the tissues with the blade portion to expose the selected vertebral area. This method offers the advantages of secure retraction during further surgery, so that no blood vessels, nerves, or other structures are damaged by the retractor instrument, additional instruments, or accidental impact during the surgery.

BRIEF DESCRIPTION OF THE DRAWINGS

These and other features and advantages of the present invention will be better understood by reference to the following detailed description and accompanying drawings wherein:

FIG. 2 is a side elevational view of the embodiment of the retractor of FIG. 1.

FIG. 3 is a front elevational view taken on line 3—3 of FIG. 2.

DETAILED DESCRIPTION

Figure 1:
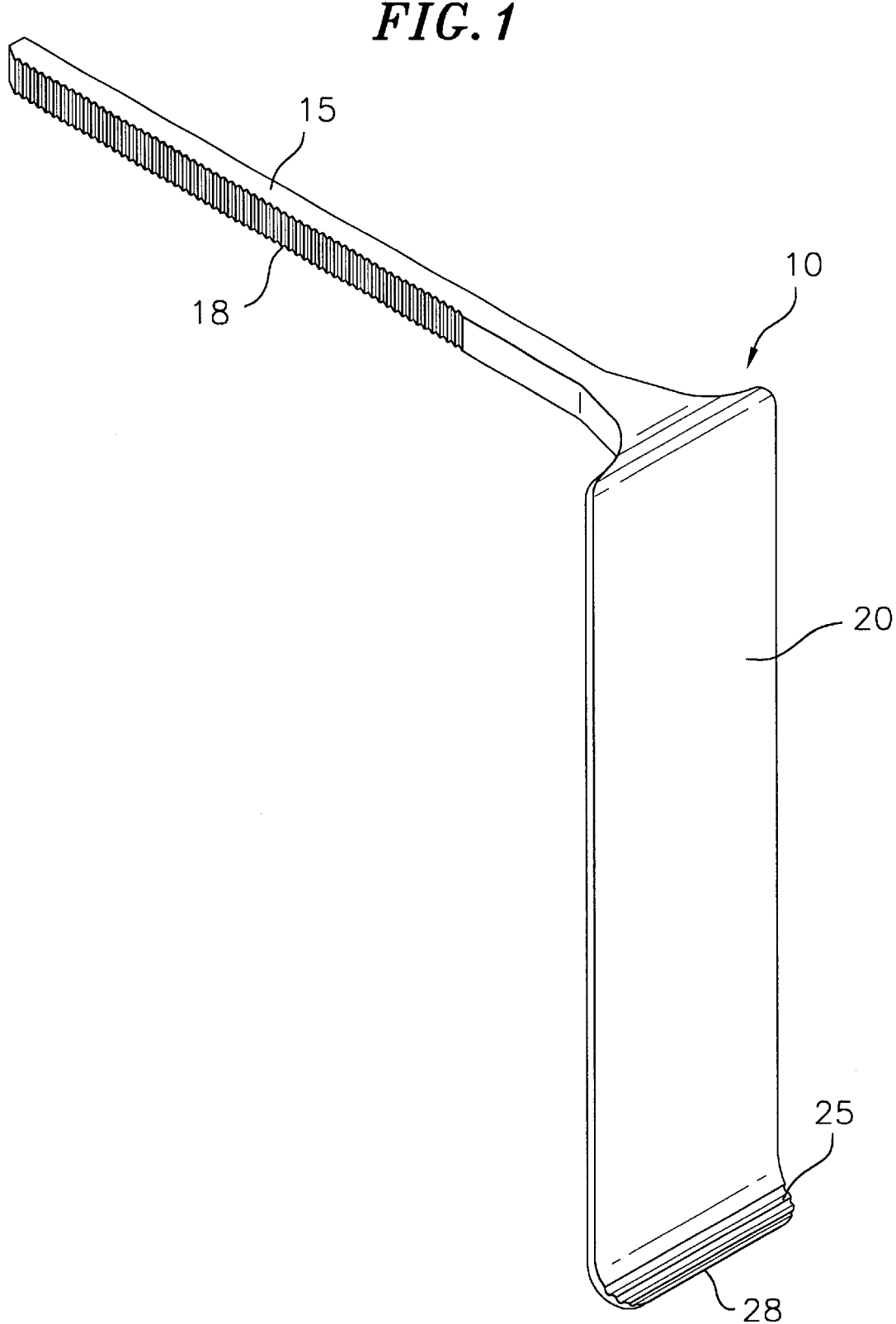
FIG. 1 is a perspective view of one embodiment of a retractor according to principles of this invention.

The retractor blade and procedure of the invention demonstrate a novel approach to preparing any anterior lumbar region exposure. They are particularly well suited to surgeries needing only a small field, such as anterior fusions of two vertebrae from L2 to S1, for example. The inventive surgical approach to the lumbar area is rapid, requires only a small skin incision, and it does not damage the rectus muscles or penetrate the peritoneum, decreasing patient discomfort and recovery time. The instrument of the invention is a retractor specially designed to maximize the size of the surgical field and provide considerably improved stability of the retractor under the relatively high pressure/tension often needed to maintain clear access to the spine. This increased stability and the width and other parameters of the retractor blade also leads to a greatly decreased risk of retracted tissues slipping into the surgical field and being injured. The retractor and/or surgical method can be used in either human or veterinary patients.

The Retractor Blade

FIGS. 1 through 4 show various embodiments and configurations of a retractor 10 of this invention. The retractor 10 includes a long, narrow, rigid handle portion 15 and an elongated thin, flat blade portion 20 which is shown extending generally at a right angle from an end of the handle portion. The term "retractor" and "retractor blade" may be used interchangeably herein, and is intended to mean the handle 15 and blade 20, but it is understood that the term "retractor" may also be used in more general contexts to include related apparatus used to stabilize the retractor handle/blade portion, such as a self-retaining retractor system like the Bookwalter system (Codman and Shurtleff, Inc.) or the Omni Retractor (Minnesota Scientific, Inc.).

The retractor 10 is preferably made of metal, but can be fabricated of any other suitable material (e.g., plastics). The material requirements are similar to those for any surgical instrument, e.g., that it can be cleaned and sterilized for reuse by standard methods (e.g., sonication, autoclaving, UV irradiation), it can withstand the forces put upon tools of this sort (e.g., the elastic forces and weight of tissues retracted out of their natural position), and that it be economical to produce commercially. For the retractors of this invention, preferred metals for fabrication are stainless steel, aluminum, or other alloys. Alternative embodiments (e.g., single use disposable instruments) are also within the scope of the invention, and the inventive features of the retractor can be manufactured into any retractor blade or self-retaining retractor system suitable for anterior retroperitoneal access surgery. The blade portion of the retractor can be formed of a single piece of suitable material, molded, or made of two or more separate pieces of the same or different material which are then assembled (e.g., the handle is fastened to the blade) by means of, for example, solder or welds, glue, pins, bolts, screws, or the like. The blade portion of the retractor can be provided in a configuration suitable for use, or it can be provided in another configuration (e.g., flat or linear) and be bendable into a configuration suitable for use (described more fully below). Thus, the blade portion of retractors of the invention may be malleable or rigid. Preferably, only the blade portion of the retractor is malleable, if any part of the retractor is malleable.

Referring again to FIGS. 1–4, the handle 15 is square in cross section, although any cross-sectional shape may be used. Likewise, the handle 15 shown in FIG. 1 has ridges 18 which serve to more stably anchor the handle in a clamping device, if one is used; or conversely the ridges may prevent slipping of the retractor if held by the digits of a hand. The ridges 18 can be uniformly sized or not, and can be positioned straight up or oriented at an angle (e.g., in a saw-toothed arrangement) to preferentially reinforce the handle against slipping in a particular direction, or to allow for adjustment of the position of the handle (e.g., by ratcheting) in a retractor stand. The handle 15 shown in FIG. 1 is straight, for easier insertion into a standard ring stand, arm, or other clamping device by means of an adapter, as is common in surgical devices such as the Bookwalter retractor system and others (see, e.g., U.S. Pat. Nos. 3,998,217, 4,813,401, 5,025,780, 5,052,373, 5,688,223, 5,728,046, 5,795,291, 5,902,233, 5,944,658). However, the handle 15 does not need to be straight, and may be curved, or of any shape and dimension to adapt to the preference of the user (for example, for holding in the hand, to fit into specialized retractor devices, etc.). The handle may be of any length, but is preferably between about 1–20 inches in length, more preferably between about 6–8 inches in length. Likewise, the thickness of the handle may vary, and need not be uniform along the entire length of the handle. In a preferred embodiment for use clamped in a retractor stand, the handle is about 6.5 inches long and about 1 cm in diameter.

The blade portion 20 is generally initially planar, or substantially flat, and connects to one end of the handle 15 at one end of the blade. In rigid embodiments of the retractor, the blade portion is substantially planar, while in malleable embodiments, the bending of the blade portion may render it less planar and more curved. The blade may be of any width, but is preferably from about 1 cm to 15 cm, more preferably from about 2 cm to 6 cm wide to prevent damage that wider blades can cause. The length of the blade is likewise variable. The best length depends upon the size of the patient the retractor is used on. For example, a very thin or small person may require only about 5 cm of blade length or less to restrain tissues during surgery, while an obese person might require 20 cm or more of blade length for secure retraction. Thus, the retractor can have blades of varying lengths, preferably at least about 2 cm to 30 cm long, more preferably at least 5 cm to 20 cm long. It is understood that malleable retractor blades need not have as much variability in length, because they can be bent along the blade portion into the desired length by the user as needed. Preferably, malleable retractor blades are longer, between about 7.5 to 30 cm long. The thickness of the blade portion is preferably less than about 0.5 cm, more preferably less than about 0.25 cm.

Figure 4:
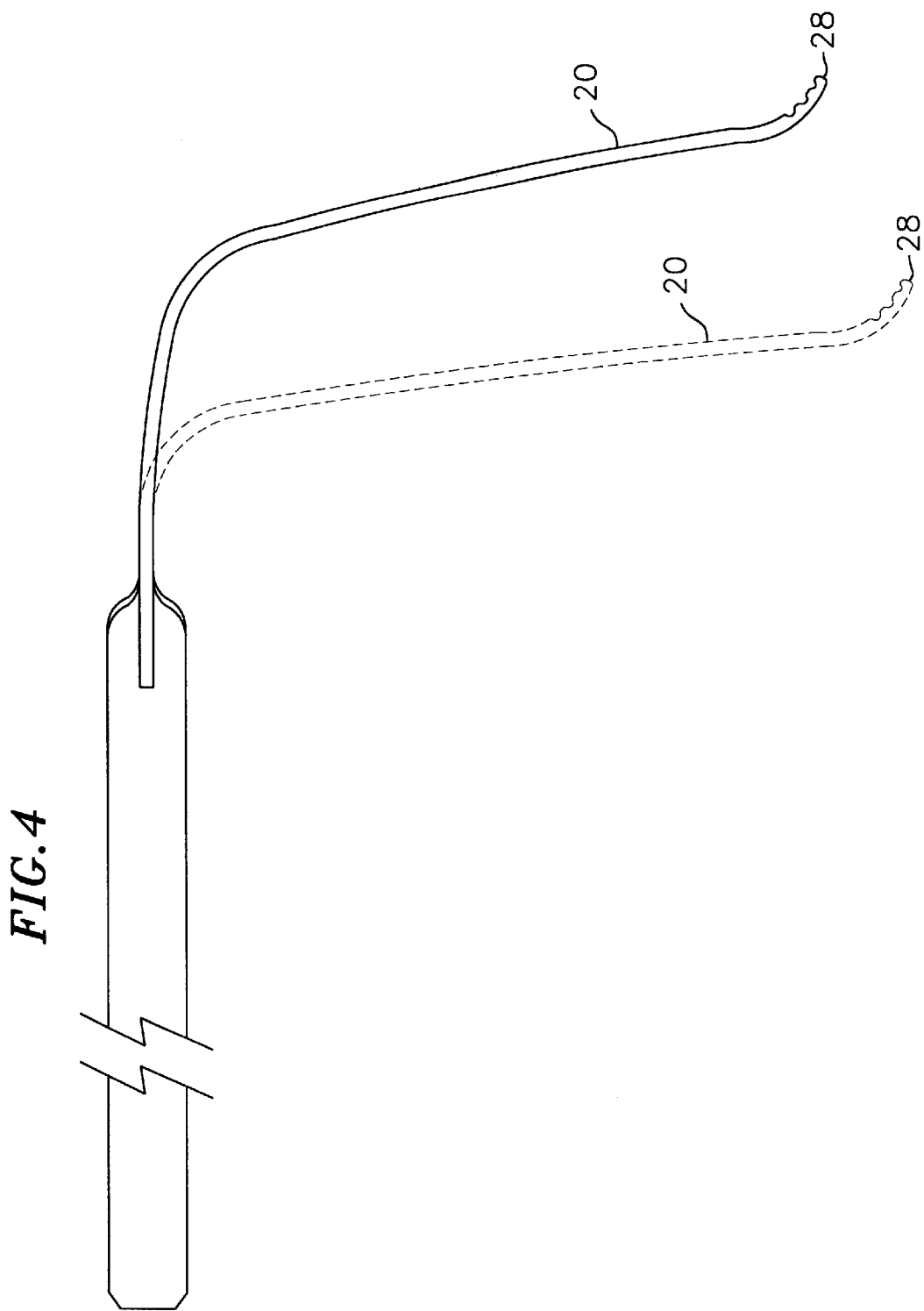
FIG. 4 is a side elevational view of a malleable embodiment of the retractor, showing the blade in two of many possible operative configurations (solid and dashed lines).

The blade 20 and the handle 15 can be joined in any configuration, but when configured for surgical use, they will be at an angle θ of less than 180° with respect to each other, preferably at an angle θ of about 90° (about a right angle, see FIG. 2) and substantially the entire blade will extend below an axis aligned with the handle. For malleable blades such as shown in FIG. 4, the angle when the retractor is configured for use will not likely be the same over the length of the blade portion with respect to the handle, because it will probably have a controlled curvature over the length of the blade portion from being bent by the user. The curvature is preferably minimized, with no part of the blade protruding above or below about 2.5 cm from a line drawn from the handle (or beginning of the bent portion in a malleable retractor) to the portion of the blade just before the lip starts to curve, more preferably less than about 1.5 cm.

Figure 6:
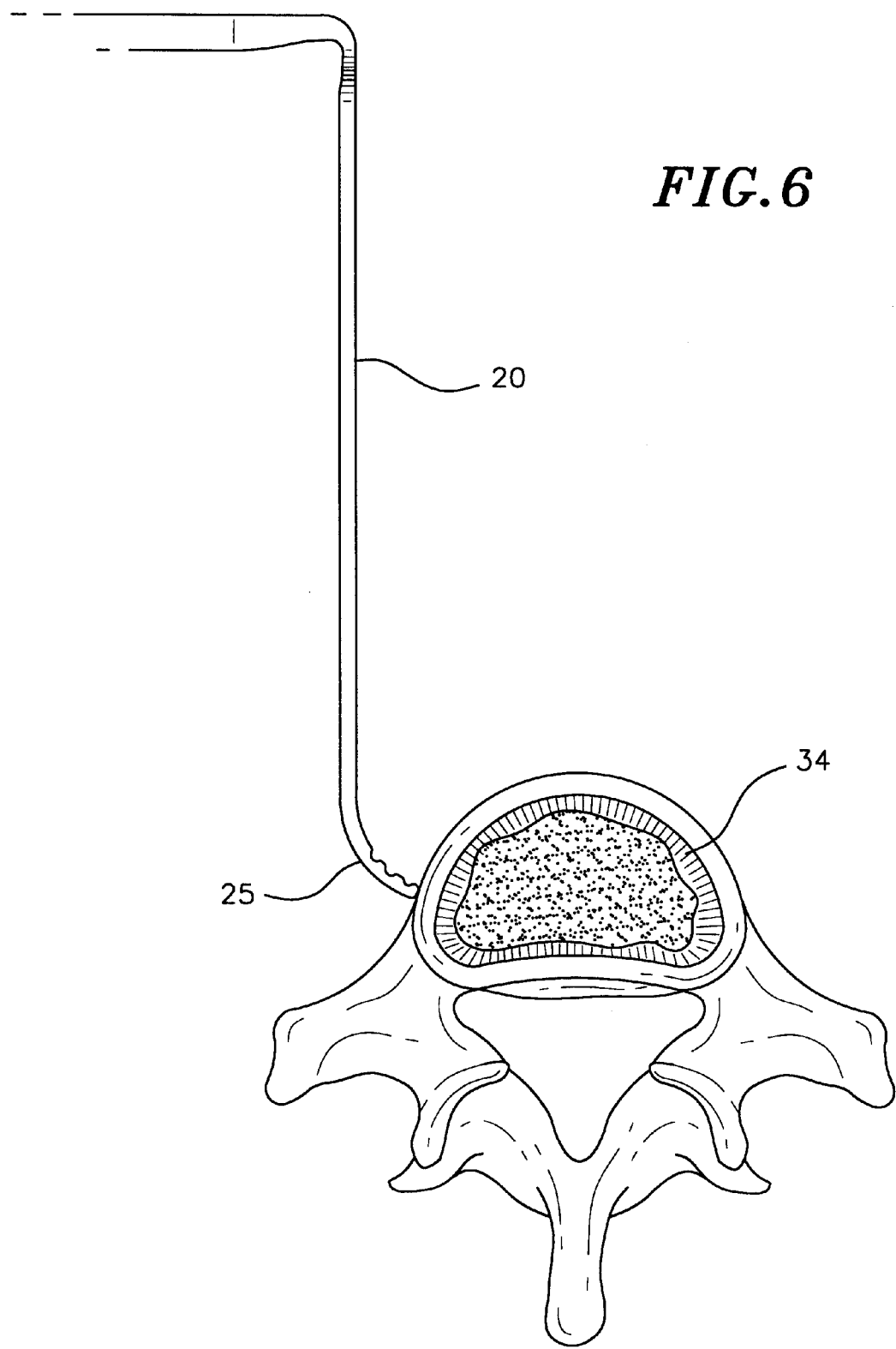
FIG. 6 is a schematic representation of a retractor of the invention in use, engaged against a lumbar vertebral body.

Referring to FIGS. 1, 2, and 4, free the end of the blade 20 has a curved lip 25 having a leading edge 28 which is the distal-most edge of the blade (with respect to the (proximal) handle) and the end of the curved lip portion 25. When the retractor 10 is in a usable configuration (having an angle θ less than 180°), the curve of this lip is outward, or in a direction roughly opposite to the direction of the handle (see FIGS. 2 and 4 (silhouette)). The orientation of this lip is critical. The lip generally will comprise no more than between about 0.5 to about 5 cm of the blade length, more preferably about 1 cm to about 1.5 cm of the blade length, most preferably about 1.25 cm of the blade length. The lip curves out of the general plane of the substantially flat blade surface preferably no more than about 5 cm (vertical height), more preferably no more than about 2 cm, most preferably no more than about 0.3 to about 0.7 cm. The curve of the lip is preferably relatively shallow (e.g., preferably having a radius of curvature of between 1 cm and 3 cm and curving over about 20–50° of the circle of curvature, more preferably having a radius of curvature between about 1.5 cm and about 1.8 cm and curving over about 25–40° of the circle of curvature). The curvature is sufficient to allow the lip 25 to wedge under or against the general curvature (in shape and degree) of the body of the lumbar vertebrae 34 when placed generally perpendicular to a vertebra and/or disc as it lies in the body aligned in the spine (FIG. 6). The lip 25 serves to lodge the retractor firmly into position when it is deployed against the vertebral body 34 or disc. This minimizes the risk of the retractor slipping during surgery. This is desirable since slippage can lead to retracted tissues entering the field of surgery and being damaged. Consequences of such damage are permanent nerve injury, hemorrhage, ureter or organ injury, etc. These injuries are the most common complications of anterior lumbar surgery, and the retractor blade of the invention greatly reduces the risks, simply by providing greatly improved stability during use.

In a preferred embodiment, the side of the lip 25 opposite the handle (e.g., the side that will face the vertebral body during use), and/or the leading edge 28 of the lip have a roughened surface. This roughness adds additional purchase or "stickiness" to the interaction between the retractor and the bone surface, reducing the possibility of slippage even further.

Surgical Approach to the Anterior Lumbar Region

The surgical method of the invention is an anterior retroperitoneal rectus muscle sparing approach to the spine in the region of lumbar vertebra 2 (L2) to sacral vertebra 1 (S1). In addition to the advantages of leaving the rectus muscle intact, the method minimizes damage to peritoneal structures and blood vessels associated with the lumbar region. This method exposes the spine in the specific region desired, generally pairs of vertebra (e.g., L2–3, L3–4, L4–5, or L5–S1), for surgical intervention, such as disc repair, removal, and/or vertebral fusion. The method can be adapted to expose more vertebrae if desired. If pairs of vertebrae are exposed, as is usual, the method requires only an exceptionally small skin incision, one of many advantages of the method.

In preparation for the procedure, the patient is placed in the supine position on a Jackson or other X-ray table with an inflatable bag under the lumbar region. Inflation of the bag will allow for extension of the spine at the time of discectomy and graft placement, and the X-ray table allows radiographic images to be taken during the procedure to ascertain the position of the surgeon along the spine.

Generally, the approach surgeon stands on the left and the assistant on the right. The approach to the spine is preferably from the patient's left side to avoid the vena cava, which anatomically lies to the right of the spine. The incision is begun at the midline of the body and carried transversely to the lateral edge of the rectus muscle. The level of the incision in the cranio-caudad plane depends on the level of the spine approached, and will generally be in the regions shown in FIG. 5.

The incision for L5–S1 access is usually at the junction of the lower and middle thirds of the distance between the umbilicus and the symphisis pubis. This incision, however, needs to be moved caudad or cephalad depending on the angle of L5–S1 as seen on a lateral plain X-ray film. In other words, the degree of pelvic tilt, lordosis, or other individual variability must be considered. Proper placement of this small incision by the approach surgeon is crucial to the spinal surgeon in placing the working sleeves for vertebral fusion operations at the proper angle parallel to the vertebrae.

Figure 5:
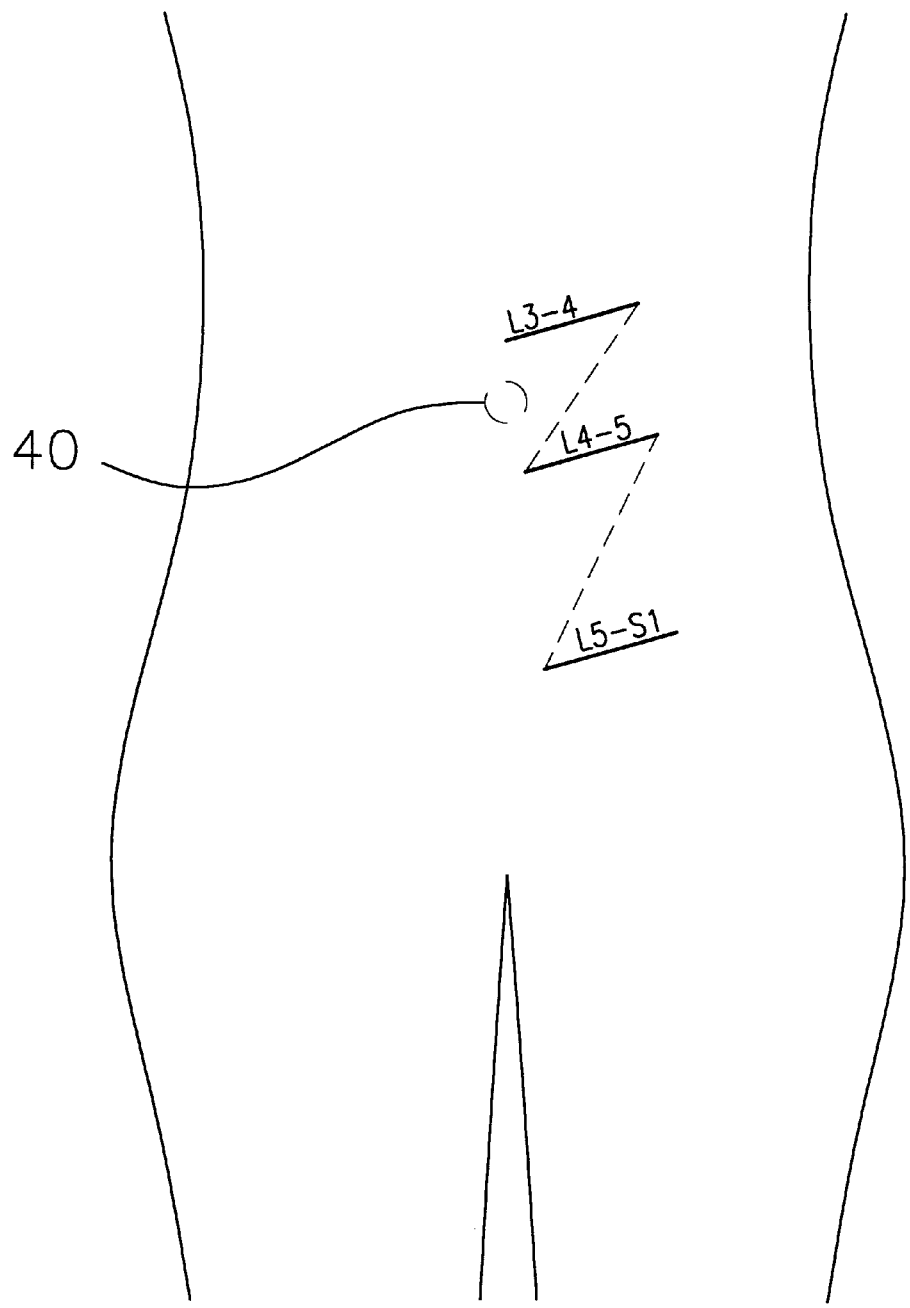
FIG. 5 is a diagram of the common incision sites to access lumbar vertebrae 3 and 4 (L3–4), lumbar vertebrae 4 and 5 (L4–5), and lumbar vertebra 5 and sacral vertebra 1 (L5–S1).

For L4–5 access, the incision is placed just below the umbilicus, and for L3–4, the incision is placed just above the umbilicus 40 (FIG. 5). For L2–3 access, the incision is placed about 5 cm above the umbilicus. Lateral X-rays can be used to evaluate the placement of the skin incision at the upper levels as well, since there is frequently some anatomical variation that may influence the placement of the incision 1 or 2 cm higher or lower. For two- or more-level exposure (e.g., more than one disc to be exposed), the incision should be more oblique, starting at the level of the lower disc and ending at the level of the upper disc. If the midline of the body is the reference line (0° toward the head, 180° toward the feet), a single-level exposure will require an incision of about 70–90°, preferably about 80°. A two-level exposure will require an incision of about 35–55°, preferably about 45°, and a three or more level exposure will require an incision of between about 10–45°, preferably between about 25–35°. The incisions using the method of the invention are smaller than those normally used for similar exposures.

The incision is carried to the anterior rectus sheath using electrocautery and the subcutaneous portion of the incision is carried beyond the ends of the skin incision both medially and laterally. This will expose a subcutaneous area beyond the midline as well as the external oblique aponeurosis. The rectus sheath (or fascia) is incised from about 1 cm to the right of the midline to the edge of the rectus laterally. The anterior rectus sheath is then elevated anteriorly away from the muscle belly for a distance of about 6 to 8 cm both superiorly and inferiorly to allow for full mobilization of the rectus muscle. The muscle is freed from any connective tissue all around the body of the muscle. Posterior dissection of the muscle is carried out bluntly, taking great care to avoid injury to the inferior epigastric vessels, which run along the undersurface of the muscle and must be elevated with the muscle and retracted with it using an appropriate curved retractor. Preservation of this neurovascular bundle is essential in preventing denervation of the muscle. Because the muscle is freed and mobilized in both directions from the single incision point of the fascia/sheath, no additional incisions of the sheath are needed, unlike prior methods. The rectus muscle mobilized in this way can easily be retracted medially or laterally, and no damage has been done to the muscle itself, making the patient's recovery much faster and less painful.

With the rectus muscle initially retracted medially, the posterior sheath or transversalis fascia is carefully incised about 4–5 mm until the peritoneum is seen to shine through. The edges of the cut fascia are grasped with a hemostat, then lifted away and very carefully dissected from the peritoneum and incised as far inferiorly and superiorly as possible. This layer can be quite tenuous and care must be exercised to prevent peritoneal lacerations. The peritoneum will now bulge upward. Using a finger, the surgeon next carefully pushes the peritoneum posteriorly at the edge of the rectus fascia and slowly develops a plane between it and the undersurface of the internal oblique and transversus muscles and fascia. This opening leads into the retroperitoneal space. Careful blunt finger dissection is continued posteriorly and then the surgeon should begin pushing medially to elevate the peritoneum away from the psoas muscle. If the peritoneum is accidentally entered at any point, the tear should be repaired with absorbable suture material at that time. Delaying this repair will only lead to major peritoneal repairs later on. The surgeon should be careful not to enter the retropsoas space at this point as this will lead to unnecessary bleeding in a blind pouch. The genito-femoral nerve can be easily identified over the psoas. The ureter can usually be identified as the peritoneum is lifted away from the psoas. Both of these structures should be protected from injury. Once the psoas is identified, the surgeon should palpate medially to feel for the disc space and body of the vertebrae, and the iliac artery. At this point, the entire hand may be inserted (if the size of the incision allows) and a fist made in the retro-peritoneal area. The peritoneum is elevated away in all directions by sweeping the area with the closed fist up and down. A Balfour retractor or the like with appropriately deep blades is then inserted to keep the incision open in the cranio-caudad plane. A dry lap sponge tucked above the upper blade of the Balfour is helpful in keeping retroperitoneal fat from creeping down and obscuring the field. A Harrington retractor or similar is used to keep the peritoneal contents away from the vessels and allow further dissection.

For operations on L5–S1, the dissection is then carried anterior and medial to the left iliac artery with the Harrington retractor preferably placed into that plane to elevate the peritoneal contents. The disc between L5–S1 is palpated and the dissection is carried toward it with blunt dissection between the iliac vessels and below the aortic bifurcation. The iliac vein is seen deep to the artery and swept towards the left to expose that side of the disc. Dissection towards the right exposes that side of the disc and a retractor of the invention, a reverse-lipped, optionally malleable retractor (described above) can be used to maintain exposure to that side by anchoring the lip on the lateral aspect of the spine. The iliac vessels are not usually visualized on the right side. The middle sacral vessels can be taken between clips or ligatures, keeping cautery to a minimum, particularly in males, to preserve the superior hypogastric plexus fibers. The left iliac vein sometimes needs to be widely mobilized to allow placement of the reverse-lipped, malleable retractor against the left lateral edge of the spine. The Bookwalter or similar retractor is used to keep two reverse-lipped (malleable) blades in place during discectomy and placement of hardware, bone grafts, etc.

For operations on only L4–5 or for operations that combine L4–5 with either L3–4 or L5–S1, the ileo-lumbar vein(s) must be ligated and cut as they serve as a tether preventing mobilization of the iliac vein away from the anterior surface of the spine and thus prevent proper exposure. A Deaver, Harrington, or similar retractor is placed into the plane above the artery to elevate the peritoneal contents away. The surgeon then dissects bluntly just above the iliac artery and moves the retroperitoneal tissues away from the artery. The entire length of the common and external iliac arteries are exposed as far distally as possible, and then a careful blunt dissection is started along the lateral edge of the artery. This will expose the left common iliac vein just underneath the artery. The dissection is continued posteriorly to identify the ileo-lumbar vein(s), which crosses the body of L5 and dives into the left paraspinous area. Variations in the formation of the common iliac vein and the lumbar veins are common and great care must be exercised in order to identify, ligate and transect these veins and avoid accidental avulsion or other trauma. Ligation should be carried out in place prior to transection and not too close to the ligated vein's junction to the iliac vein itself in order to avoid injury to the iliac vein's sidewall. For any operation that involves L4–5, these maneuvers are imperative to safely mobilize the interfering vasculature away from the surgical field.

The left iliac vein and artery can now be separated away from the spine using gentle peanut sponge, fingertip and blunt elevator dissection. In most patients the vein "peels" away from the anterior surface of the spine easily. In some patients, however, there is intense inflammatory reaction in the plane between the vein and the anterior longitudinal ligament, especially when osteophytes are present; so the dissection can be quite difficult and tedious. All the vascular structures are thus swept from left to right to provide adequate visualization of the disc(s) and vertebral bodies involved. Segmental vessels running across the valleys on the anterior surface of the bodies can be transected between clips and swept to the sides with blunt dissection. The surgeon should be sure to make sufficient room to get at least one finger between the common iliac vein and the anterior longitudinal ligament (ALL) in order to palpate the right lateral edge of the spine with the vessels above the finger(s). Care must be taken not to tear tissues that don't give way easily, because in doing this, the surgeon may tear lumbar veins coming in from the right side. Once this part of the exposure is completed, the retractors (e.g., Balfour and Harrington) are removed.

At this point, the dissection of the surgical field is complete, and it remains to retract the peritoneum, vasculature, and other tissues away from the spine to provide a clear exposure of the disc(s) and vertebrae of interest.

Use of the Retractor to Maintain Anterior Retroperitoneal Lumbar Exposure During Spine Surgery Preferably, a Bookwalter self-retaining retractor post and ring system (or similar arrangement) is then set up. It is understood that manual retraction can also be used with the retractors of the invention, but the use of a retractor post and ring increases the stability of the retraction, and eliminates human error/variability and reduces the risk of the retractors slipping.

The rectus muscle is now retracted laterally, rather than medially as it was for the initial dissection, in order to reduce the amount of pull on the muscle going forward with the operation. This positioning also has the advantage that the muscle is not damaged during the surgery, as prolonged retraction medially might cause.

The surgeon's hand then re-enters the retro-peritoneal space with the rectus now moved laterally, and the fingers find their way to the right side of the spine following the planes previously dissected. The retractor, either rigid or malleable, and having the small reverse lip, bent to (if malleable) or having the appropriate blade length for the patient's size, is then placed blindly onto the right side of the spine using the finger(s) as a guide to place the leading edge of the lip securely against the spine. This blade is then pushed to the right, attached to the ring of the retractor stand by standard means (e.g., a clamp or adaptor), then pushed further to elevate the vascular structures and expose the anterior surface of the spine. Once secured to the ring of the self-retaining retractor system (e.g., Bookwalter), the retractor will not move. The lip keeps the blade anchored to the edge of the spine and prevents it from slipping anteriorly once tension is applied. Without this lip, the retractor blade will not work and the risk of the retractor slipping is greatly increased.

With the rectus now retracted laterally, there will be much less resistance when pushing the retractor blade to expose the spine in a direct anterior-posterior view. A second such retractor blade is placed on the left side of the spine and attach to the ring to complete the exposure. When rigid blades are used that have about a right angle to the handle, the field is clear straight down from the retractors' insertion point. The straight approach and reliable clearance of tissue from the exposure means that a much smaller incision is necessary to allow placement of the sleeves used for disc and fusion surgery (e.g., for insertion of a threaded device or femoral ring) than if curved retractor blades are used. Occasionally, additional retractor blades need to be placed superiorly or inferiorly to complete the exposure. X-rays should be taken after the first two blades are placed so as not to obscure the field with too much hardware. With these blades well anchored to the lateral wall of the vertebrae, the spine surgeon and his assistant can now work on the disc without other hands or retractors being in the way and with relative security that vessels will not sneak around the retractors and expose themselves to injury. Utmost care, however, needs to be exercised to prevent such injuries.

For operations of L3–4 and L2–3 mobilization of the iliac vessels is usually not necessary, and only occasionally will the surgeon need to transect the ileo-lumbar vein(s) to obtain adequate mobilization. This makes approaching these two levels somewhat easier.

When approaching L4–5 and L5–S1, it is usually necessary to get to L5–S1 between the common iliac vessels and to L4–5 lateral to them. Occasionally, L5–S1 can be exposed via the lateral approach used for L4–5 if the aortic bifurcation is low in the patient. In these cases, one can actually see both levels simultaneously with only minimal adjustment of the retractor and its blades to provide optimal access. Only rarely, however, is it possible to expose L4–5 by going between the vessels after having completed the exposure of L5–S1.

Spinal surgery, such as discectomy and instrumentation can be performed after the above steps have been completed. Upon completion of the spinal procedure, the left retractor is preferably removed first, then the one on the right, and the integrity of the vessels is checked thoroughly, especially looking for arterial thrombosis or injury due to stretching.

Then all retractors and lap sponge(s) are removed and the tissues are allowed to fall back together anatomically. The individual fascial layers are then closed separately with running absorbable sutures, making sure that the anterior rectus sheath is well approximated. The posterior sheath need not be closed if it is tenuous and does not offer any significant strength to the closure. A thick, substantial posterior rectus sheath, however, should be closed. Subcutaneous tissues and skin are then closed as per surgeon's preference. No Steinman pins are ever used for retraction with this approach, as they only increase risk of vessel perforation, and the retractor of the invention is sufficient alone to hold back the tissues with the necessary level of security.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A retractor instrument for maintaining a clear surgical field, the instrument comprising:
    a handle portion; and
    an elongated blade portion having a length, and having a first end connected to the handle portion, in which essentially the entire length of the blade portion extends from the first end in a direction below an axis aligned with the handle and extends generally at an angle relative to the handle portion when the instrument is in an operable configuration, the blade portion having a second end region comprising about 15% or less of the length of the blade and spaced from the handle portion, the second end region shaped as a lip that curves in a direction away from the handle portion when the blade portion is in the operable configuration, wherein the lip projects to a leading edge spaced less than about 2 cm from a plane defined by the blade portion immediately adjacent to the curvature of the lip; wherein the lip has a has a width of at least about 2.5 cm.

2. The retractor of claim 1 wherein the blade portion is substantially flat.

3. The retractor of claim 2 wherein the angle between the blade portion and the handle is about a right angle.

4. The retractor of claim 1 wherein the blade portion and the handle portion are set at about a right angle with respect to each other.

5. The retractor of claim 1 wherein the handle is capable of being reversibly immobilized by an adaptor to a retractor ring or arm.

6. The retractor of claim 1 wherein the lip is at least about 0.5 cm long and curves at least about 0.3 cm from the plane of the blade.

7. The retractor of claim 6 wherein the lip is at least about one cm long and curves at least about 0.6 cm out of the plane of the blade.

8. The retractor of claim 1 wherein the blade is between about 2.5 and about 10 cm wide, and between about 2 and about 25 cm long.

9. The retractor of claim 8 wherein the blade is between about 2.5 and about 5 cm wide.

10. The retractor of claim 1 wherein the handle and the blade are formed as a single piece.

11. The retractor of claim 1 wherein the blade portion is formed of a malleable material that can be manually shaped.

12. The retractor of claim 1 wherein the leading edge of the lip is roughened.

13. The retractor of claim 1 wherein the lip has a radius of curvature of between about 1 cm and about 3 cm and the curve extends between about 20° and about 50° of a circle of curvature.

14. The retractor of claim 13 wherein the lip has a radius of curvature between about 1.5 cm and about 1.8 cm and the curve extends between about 25° and 40° of the circle of curvature.

15. The reactor of claim 1 wherein the second region of the blade comprises about 10% or less of the length of the blade.

16. A retractor instrument for maintaining a clear surgical field for access to an anterior vertebral region of a body, the instrument comprising:
    a handle portion; and
    an elongated blade portion having a first end connected to the handle portion, the blade portion extending generally at an angle relative to the handle portion when the retractor is in an operable configuration, the blade portion having a second end region spaced from the handle portion and shaped as a lip which curves in a direction away from the handle portion, wherein the lip projects to a leading edge spaced a sufficient distance from a portion of the blade immediately adjacent the curvature of the lip and configured so that the curved lip can engage a lateral aspect of a vertebral body or vertebral disc when the blade portion is positioned adjacent to and substantially perpendicular to the vertebra; wherein the lip has a surface facing the direction opposite the handle, and the surface of the lip is roughened.

17. The retractor of claim 16 wherein the blade portion is substantially flat.

18. The retractor of claim 16 in which the blade portion has a length sufficient to reach the vertebral region from the anterior side of the body.

* * * * *